US007391846B2

(12) United States Patent
Verdonck et al.

(10) Patent No.: US 7,391,846 B2
(45) Date of Patent: Jun. 24, 2008

(54) METHOD AND X-RAY APPARATUS FOR OPTIMALLY IMAGING ANATOMICAL PARTS OF THE HUMAN ANATOMY

(75) Inventors: Bert Leo Alfons Verdonck, Eindhoven (NL); Albert Gerrit Veldhuizen, Eelde (NL)

(73) Assignee: Koninklijke Philips N.V., Eindhoven (NL)

( * ) Notice: Subject to any disclaimer, the term of this patent is extended or adjusted under 35 U.S.C. 154(b) by 1082 days.

(21) Appl. No.: 09/966,415

(22) Filed: Sep. 28, 2001

(65) Prior Publication Data

US 2002/0054662 A1    May 9, 2002

(30) Foreign Application Priority Data

Oct. 2, 2000  (EP)  ............................. 00203396

(51) Int. Cl.
 *G01N 23/04* (2006.01)
 *H05G 1/64* (2006.01)

(52) U.S. Cl. ........................................ 378/62; 378/98.8
(58) Field of Classification Search ................ 378/62, 378/63, 4–20, 38–40, 95, 204–5, 98.8
 See application file for complete search history.

(56) References Cited

U.S. PATENT DOCUMENTS

| 4,349,917 | A |   | 9/1982  | Moore ........................... 378/24 |
| 4,920,573 | A | * | 4/1990  | Rhodes et al. ............... 382/131 |
| 4,942,596 | A | * | 7/1990  | Eberhard et al. ............. 378/109 |
| 5,365,562 | A | * | 11/1994 | Toker et al. .................... 378/62 |
| 5,369,678 | A | * | 11/1994 | Chiu et al. ...................... 378/62 |
| 5,483,960 | A | * | 1/1996  | Steiger et al. ................ 600/425 |
| 5,568,384 | A | * | 10/1996 | Robb et al. ................... 715/532 |
| 5,577,089 | A | * | 11/1996 | Mazess ........................... 378/54 |
| 5,696,807 | A | * | 12/1997 | Hsieh ........................... 378/109 |
| 5,946,370 | A |   | 8/1999  | Adler et al. ...................... 378/4 |
| 6,215,846 | B1| * | 4/2001  | Mazess et al. ................. 378/62 |
| 6,320,928 | B1| * | 11/2001 | Vaillant et al. .................. 378/4 |
| 6,366,800 | B1| * | 4/2002  | Vining et al. ................ 600/425 |
| 7,046,830 | B2| * | 5/2006  | Gerard et al. ................ 382/128 |

FOREIGN PATENT DOCUMENTS

| WO | WO9410908  |   | 5/1994 |
| WO | WO 98/24063 | * | 6/1998 |

* cited by examiner

*Primary Examiner*—Edward J. Glick
*Assistant Examiner*—Anastasia Midkiff

(57) ABSTRACT

A method and an X-ray apparatus for imaging anatomical parts of the human anatomy, in particular for imaging the human spine. In order to improve the quality and the diagnostic value of projection images of the anatomical parts the invention acquires at least one initial projection image of at least the region of interest of the anatomy, to determine the positions and/or orientations of the anatomical parts in the region of interest from the at least one initial projection image and/or from other sources of information, to determine the optimum imaging parameters for the anatomical parts from their positions and/or orientations, and to acquire images of the anatomical parts while using the optimum imaging parameters. The complexity of the scene and the mixture of over-projecting structures limiting the diagnostic reliability of the projection images are thus taken into account. In a preferred embodiment a scanning trajectory is determined while using the information of the at least one initial projection image along which the source-detector unit is moved while acquiring the projection images of the spine.

14 Claims, 4 Drawing Sheets

METHOD AND X-RAY APPARATUS FOR OPTIMALLY IMAGING ANATOMICAL PARTS OF THE HUMAN ANATOMY

FIELD OF THE INVENTION

The present invention relates to a method for imaging the anatomical parts of the human anatomy by means of an X-ray apparatus as well as to an X-ray apparatus having an X-ray source and an X-ray detector facing the X-ray source, the X-ray source and the X-ray detector being movable with respect to each other and with respect to the patient so as to enable the acquisition of projection images of the anatomy from different positions and/or orientations.

BACKGROUND INFORMATION

A method for imaging the human spine by means of a CT system is known from U.S. Pat. No. 5,946,370. Therein two-dimensional data from CT scout images are combined with three-dimensional information from CT scans using simple modelling of vertebrae. It is often, however, preferred to image the spine of the patient in an upright position. A CT system cannot be used in such a case.

In digital X-ray imaging a composition of an image from sub-images is generally used to form a composite image of an elongate scene which is too long to be reproduced in one operation. In medical X-ray diagnostics such a situation occurs notably when an image of the spinal column is made. Using a contemporary digital X-ray examination apparatus it is difficult or even impossible to form an X-ray image of the complete region of the spinal column of the patient to be examined in one exposure. A number of successive X-ray images of portions of the region to be examined are formed, which images together cover the entire region. A method of this kind is also called the translation reconstruction technique and is known from EP 0 655 861 A1. Such a technique can also be used for imaging other parts of the human anatomy.

Due to the complexity of the scene (around the spinal column there are located other portions of the body like the thorax, rib cage, abdomen, head and neck which are also imaged when imaging the spine) and due to the mixture of over-projecting structures, projection images are often of low quality and limit the diagnostic reliability. Even when a normal-curved spine is imaged there are portions of the spine where neighbouring vertebrae may overlap each other in projection images. Furthermore, when the spine of a patient shows an abnormal curvature, e.g. an exagerated forward curvature (lordosis), an exagerated backward curvature (kyphosis) or a lateral curvature (scoliosis), such overlapping structures occur even more in the curved portions of the spine, thus reducing the quality of the projection images further. Another problem arises when the vertebrae of the spine exhibit an axial rotation. Consecutive projection images taken from the same direction will then show axially rotated vertebrae from different angles, thus reducing the diagnostic value of these images.

The translation reconstruction technique gives easy access to digital overview images of a large part of the human anatomy like the spine. Additionally, fluoroscopy can be used for optimum positioning of the patient and the collimators of the X-ray apparatus. However, much of the information contained in this fluoroscopy data currently is not used for the planning and optimizing of the real acquisition of images of the anatomical parts.

OBJECTS AND SUMMARY OF THE INVENTION

It is, therefore, an object of the invention to provide a method and an X-ray apparatus for imaging the anatomical parts that offer a better image quality and improve the diagnostic value and accuracy of the images.

It has been recognized according to the invention that information contained in at least one initial projection image can be used to reposition the X-ray apparatus automatically for subsequent optimum imaging of the region of interest of anatomical parts. This means that the information contained in the initial projection image is used to determine the optimum imaging parameters like position, direction, collimation or exposure parameters for the anatomical parts from their position and/or orientation in the initial image. Such determination of the optimum imaging parameters can be done for each single anatomical part or for groups of anatomical parts. Thereafter images of single parts or groups of parts can be acquired while using the optimum imaging parameters, and the images can be displayed separately, i.e. successively or side-by-side at the same time, or can be combined according to the translation reconstruction technique, thus forming a (curved) composite image, e. g. of the complete spinal column (if the acquisition trajectory allows so). In order to find the optimum imaging parameters, the positions and/or orientations of parts or groups of parts are determined in the initial projection images by means of known methods.

Additionally or alternatively to the information contained in the at least one initial projection image, other sources of information can be used to determine the positions and/or orientations of the anatomical parts of interest. Such sources of information can be general knowledge about the anatomy, in particular knowledge about the positions and/or orientations of an average anatomy or about special features of an abnormal anatomy, and also knowledge from previous examinations and/or images of the same patient. Other knowledge about the patient, like weight and/or height, can be used as another source of information.

In a preferred embodiment the optimum exposure and/or collimator settings are determined from the positions, orientations and/or the appearance of the anatomical parts in the at least one initial projection image. In this embodiment first a complete scan or a fluoroscopy series which can selectively be reconstructed into an overview image can be acquired, each image then retaining all acquisition settings. After having indicated the parts of interest, e.g. the apex vertebrae of a scoliotic curve of the spine, the X-ray apparatus can then automatically acquire snapshots of all parts of interest. It can be translated automatically to align each part with the line-of-sight or it can be zoomed in for optical magnification by reducing the source-object distance or by increasing the detector-object distance. Furthermore, the collimator can be adjusted to irradiate only the parts of interest. It can be radiated with the optimal exposure settings as learnt from the initial acquisition exposure settings and the resultant contrast, noise and/or blackness of the initial image. This will result in optimally positioned, zoomed and contrasted snapshots of individual parts of interest.

Alternatively, a frontal view image of the anatomy, preferably with extremely low X-ray dose, is acquired first. Therein the region of interest is drawn, e.g. the envelope of the spinal column. Thereafter, the region of interest is scanned optimally, which means that the start and stop positions, the collimation and the exposure control are optimized for the content of the region of interest. This may be a compromise for a given certain target region, or allow really local adaptations, and perhaps while varying these parameters smoothly from one image to the next. This greatly improves the image quality of the region of interest while reducing the overall X-ray dose to the patient.

Preferably, the optimum projection lines for acquiring projection images of the anatomical parts are determined from the positions and/or orientations of the anatomical parts. In particular, if the anatomy, e.g. the spinal column, is deformed, it is beneficial to adapt the projection lines to this deformation. Depending on the extent of deformation the lateral and/or frontal tilt angle of the anatomical parts may be different for each anatomical part and/or an axial rotation of the anatomical parts, e.g. the vertebrae may occur. This requires adaptation of the projection line to the specific position and/or orientation of an anatomical part. Preferably, this is done for each anatomical part.

Preferably the at least one initial projection image is taken as a lateral or a frontal image. The selection of the direction of the initial projection image depends on the direction of the projection images to be taken and on the specific curvature of the anatomy to be examined. A specific frontal and/or lateral image is then used in another preferred embodiment to determine the frontal and/or lateral spine axis and/or the frontal and/or lateral tilt angles of the vertebrae.

In still another preferred embodiment the at least one initial projection image is an overview image reconstructed from at least two projection images. Preferably, this overview image is determined from a series of fluoroscopy images of known 3D position. The overview image, which may be a lateral or a frontal overview image will then be used to determine the positions and/or orientations of anatomical parts in the region of interest.

The method according to the invention is preferably used for imaging the human spine, comprising the steps as claimed in claim 8. The information contained in the at least one initial projection image is then used to reposition the X-ray apparatus automatically for subsequent imaging of the region of interest of the spine or specific parts thereof. Optimum imaging parameters are thus determined for the vertebrae from their position and/or orientation in the initial image. This determination of the optimum imaging parameters can be done for each single vertebra or groups of vertebrae. Thereafter images of single vertebrae or groups of vertebrae can be aquired using the optimum imaging parameters, and a (curved) composite image of the complete spinal column can be aquired. To find the optimum imaging parameters the positions and/or orientations of vertebrae or groups of vertebrae are determined in the initial protection image(s) by means of known methods.

In a preferred embodiment, the spinal axis line is determined from the at least one projection image and the projection lines are set perpendicular to the spinal axis line. Alternatively, the tilt angles of the vertebrae are determined from the initial projection image, and the projection lines are set parallel to the end plates of the vertebrae. Preferably one projection line per vertebra is determined in these preferred embodiments. Depending on the acquisition of projection images from the lateral or frontal direction, the frontal or lateral spinal axis line and/or tilt angle of the vertebrae are determined from the initial projection image. This information is used to angulate dynamically so as to align with the projection lines for each vertebral body during the frontal or lateral scan. This results in a series of lateral and/or frontal projection images that are all as parallel as possible to the end plates of the vertebrae, and hence in a better vertebral body image quality. For the lateral images this alleviates the well-known problem of low quality lateral images for patients with large frontal curves that are due to disturbing overprojections and due to the fact that the projections are far from parallel to the vertebral end plates.

In an advantageous embodiment the axial rotation of the vertebrae is determined from the initial projection image, and the projection lines are set by utilizing the axial rotation of the vertebrae. Using this information, the source-detector unit is rotated while acquiring projection images of the vertebrae so as to compensate for axial rotation. This results in views of vertebrae with no or only a small axial rotation, i.e. real frontal views with respect to a local vertebrae coordinate system. Acquisitions perpendicular to these minimum axial rotation views will result in real lateral views. A combination of the initial axial rotation estimate and the remaining small rotation will result in more accurate axial rotation measurements.

In another preferred embodiment an optimum scanning trajectory for subsequently acquiring projection images of the vertebrae is determined. During the subsequent acquiring of the projection images the X-ray source and detector are then dynamically angulated and/or rotated to align with the optimum projection line for each vertebra, resulting in optimum projection images.

According to still another preferred embodiment a 3D spinal axis model is fitted to a pair of overview images, and an optimum scanning trajectory is determined from the fitted 3D spinal axis model. Preferably a frontal and a lateral overview image whereto the 3D spinal axis model is fitted are acquired first. The optimum scanning trajectory is a smooth trajectory that looks for a compromise of projection parameters for a series of consecutive vertebrae.

In order to determine the positions and/or orientations of the vertebrae in the initial projection image anatomical landmarks of the vertebrae, in particular the corners and pedicles of the vertebrae, are used. These pedicles can preferably be used to determine the axial rotation of a vertebral body since an assymmetry of the pedicle shadows appears in a plane perpendicular to a vertebral axis when the vertebral body is axially rotated.

Other preferred embodiments of the method according to the invention for imaging the anatomical parts, in particular pertain to the human spine.

Notably, the spinal axis line is determined from the at least one projection image and that optimum projection lines are set perpendicular to the spinal axis line. Notably, the tilt angles of the vertebrae are determined from the at least one initial projection image and that the projection lines are set parallel to the end plates of the vertebrae. Notably, the axial rotation of the vertebrae is determined from the at least one initial projection image and that the projection lines are set by use of the axial rotation of the vertebrae. Notably, the frontal and/or lateral spine axis and/or the frontal and/or the lateral tilt angles of the vertebrae are determined from a frontal or lateral initial projection image. Notably, an optimum scanning trajectory for subsequently acquiring projection images of the vertebrae is determined by angulating and/or rotating the X-ray source and detector dynamically to align with the optimum projection line for each vertebra. Notably, a 3D spinal axis model is fitted to a pair of overview images and that an optimum scanning trajectory is determined from the fitted spinal axis model. Notably, landmarks of the vertebrae, in particular the corners and pedicles of the vertebrae, are used to determine the positions and/or orientations of the vertebrae. Notably, as other sources of information for determining the positions and/or orientations of the anatomical parts general knowledge of the anatomy, knowledge from previous examinations and/or images of the same patient and/or other knowledge about the patient, like weight and/or height, is used.

The invention can in general be used for imaging different anatomical parts of the human anatomy. In particular, the invention is suitable for imaging the hip, the lower limbs, e.g. intrinsic rotation of the femur with respect to the throchanter or femur head, the knees and ankle and the rib cage. Preferably, the invention is used for imaging the human spine or parts thereof.

An X-ray apparatus according to the invention for imaging the anatomical parts of the human anatomy is claimed in claim 17 and comprises a control unit and a processing unit. It is to be understood that this X-ray apparatus can be developed further and that further preferred embodiments thereof are feasible, which further embodiments are developed in the same or similar way as described above and as laid down in the dependent claims on the method according to the invention.

These and other aspects of the invention will become apparent from and will be explained in more detail with reference to the following embodiments and the accompanying drawings, in which FIG. 1 is a side elevation of an X-ray examination apparatus for forming X-ray images in accordance with the invention;

Figure 1:
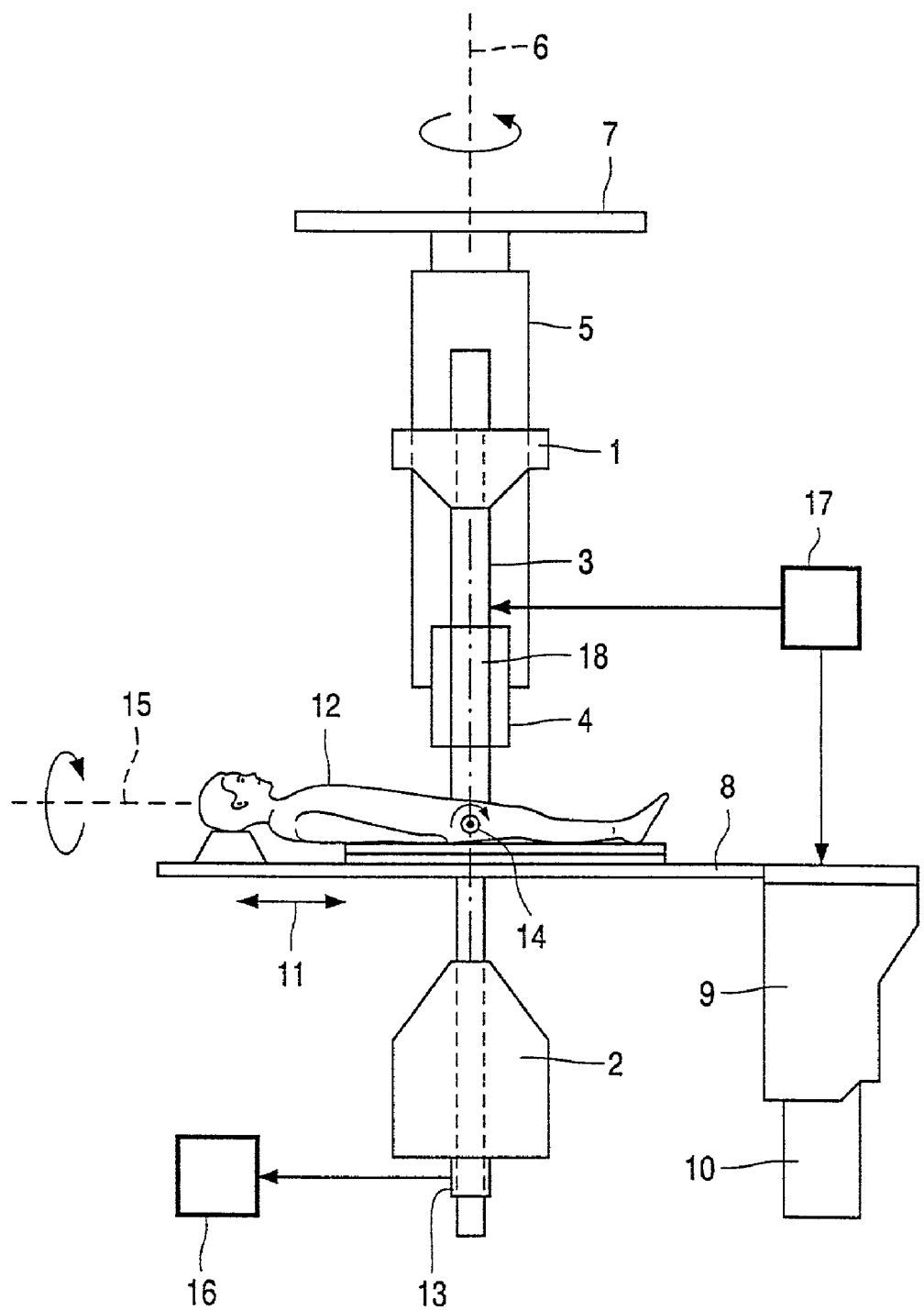

FIG. 1 is a side elevation of an X-ray examination apparatus for forming X-ray images of a patient 12 to be examined as it is known in general from EP 0 655 861 A1. An X-ray source 1 and an X-ray detector 2 are connected to a carrier 3, for example a C-arm. The C-arm 3 is movably connected to a vertical support 5 by means of a sleeve 4. The vertical support is rotatable around a substantially vertical axis of rotation 6 and is suspended from a set of rails 7 mounted on the ceiling of the room in which the X-ray examination apparatus is installed. A patient table 8 is movably connected to a frame 9 which is mounted on a column 10. The frame 9 can be moved up and down the column 10 so as to adjust the height of the table relative to the X-ray source 1. The patient table is movable relative to the frame 9 in order to enable displacement in the longitudinal direction of the patient table 8 on which the patient 12 is arranged. The C-arm 3 with the X-ray source 1 and the X-ray detector 2 can also be angulated around a horizontal propeller axis 14 and rotated around a second horizontal patient axis 15, both axes being perpendicular to each other and to the vertical rotation axis 6.

In this configuration the patient 12 is positioned on the patient table 8 during the examination and the C-arm 3 with the X-ray source 1 and the X-ray detector 2 and the patient table 8 with the patient 12 are displaced relative to one another, separate X-ray images being formed in separate relative positions. It is alternatively possible for the patient 12 to stand upright during the examination, the C-arm 3 then being moved vertically along the patient 12. This is the normal system and the normal position of the patient used for imaging the spine.

An optical image which is derived by the X-ray image intensifier 2 from an X-ray image at its entrance screen is picked up by a camera 13 and the image signal is transferred to an image processing unit 16 for further processing. Therein, several sub-images, successively taken of different portions of the spine of the patient 12, can be combined so as to form a composite image. Furthermore, image data of several X-ray images derived at different positions and from different angles of the X-ray source 1 and X-ray detector 2 with respect to the patient 12 can be combined so as to form a three-dimensional data set which can be used to calculate a desired image, for example, of a certain slice of the patient or a projection image from a certain direction. The sub-images, the composite image or other calculated images can be displayed on a display, that is either successively or side-by-side.

The X-ray apparatus, in particular the movement of the C-arm 3 and of the patient table 8, is controlled by a control unit 17. For the imaging of the human spine sub-images (projection images) are successively taken of neighbouring portions of the spine, the patient 12 either being in a horizontal position on the patient table 8 or being in an upright position. Due to several overlapping structures in the body around the spine as well as due to the overlapping of neighbouring vertebrae of the spine and due to the curvature of the spine which may be in the forward, backward and/or lateral direction, during the acquisition of the sub-images the X-ray examination apparatus is controlled such that the projection line 18, that is, the line from the center of the source 1 to the center of the detector 2, is adapted to the position of the vertebra or several vertebrae actually being imaged. This means that the C-arm 3 will be angulated around the propeller axis 14 and/or rotated around the patient axis 15 during the acquisition of the sub-images, depending on a scanning trajectory calculated in advance from at least one initial projection image, for example, a coarse overview image. This will be explained in more detail with reference to the FIGS. 2 to 5.

Figure 2A:
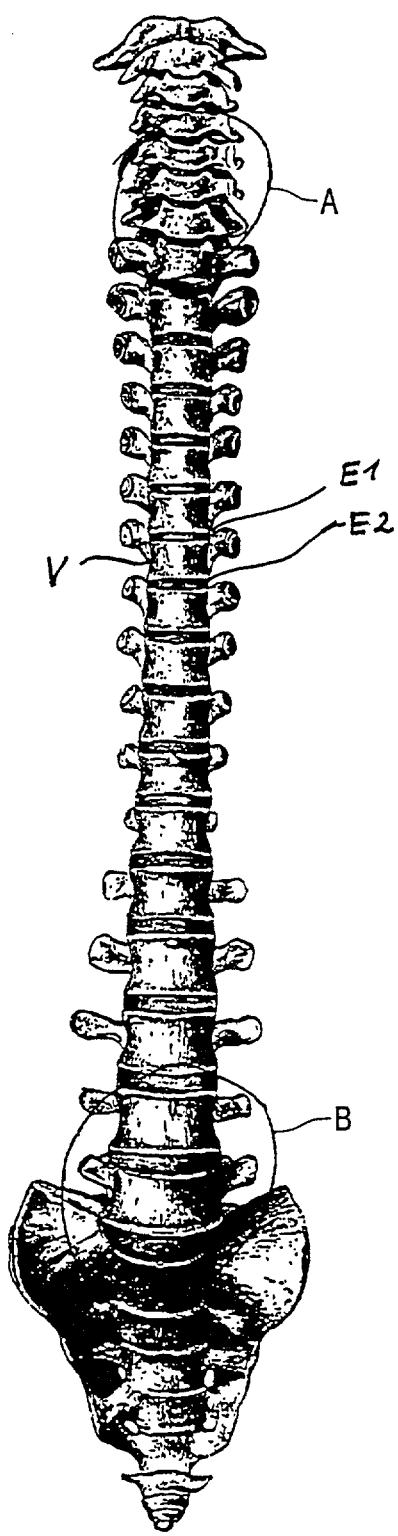
FIGS. 2A and 2B show the spinal column in a frontal view and a lateral view.
Figure 2B:
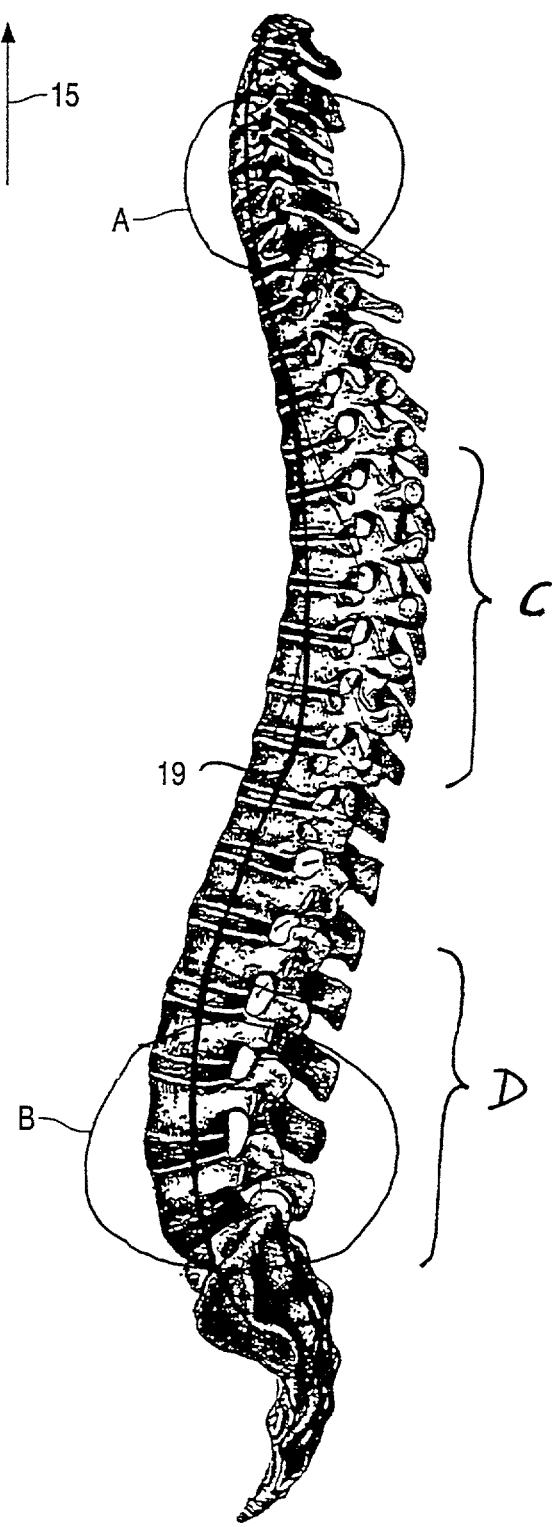

FIG. 2A is a normal frontal view of a human spinal column, and FIG. 2B is a normal lateral view thereof. As is indicated by letters "A" and "B" in these Figures, there are regions with overlapping structures, that is portions of neighbouring vertebrae may overlap in projection images taken in any horizontal direction perpendicularly to the patient axis 15. The diagnostic value of such images is thus reduced. The reason for this overlap is that in the regions A and B the endplates E1, E2 of the vertebrae V are not parallel to a horizontal plane oriented perpendicular to the patient axis 15. This problem can also occur in other regions of the spinal column, for example, in the region C where the spinal column shows a normal kyphosis or in the region D where the spinal column shows a normal lordosis. This problem becomes worse if the spinal column of a patient is even more curved, that is, showing an abnormal kyphosis or an abnormal lordosis. The spinal axis line 19 will then be even more curved as shown in FIG. 2B.

Additionally, the spinal column can be curved in the lateral direction in the frontal view and/or one or more vertebrae can be tilted in the lateral direction such that the endplates E1, E2 of a vertebra are not parallel to a lateral horizontal projection line perpendicular to the patient axis 15 and to the plane of drawing of FIG. 2B. Such tilted vertebrae in the lateral direction occur particularly when a patient suffers from scoliosis where the spinal axis line is curved in the lateral direction.

Figure 3:
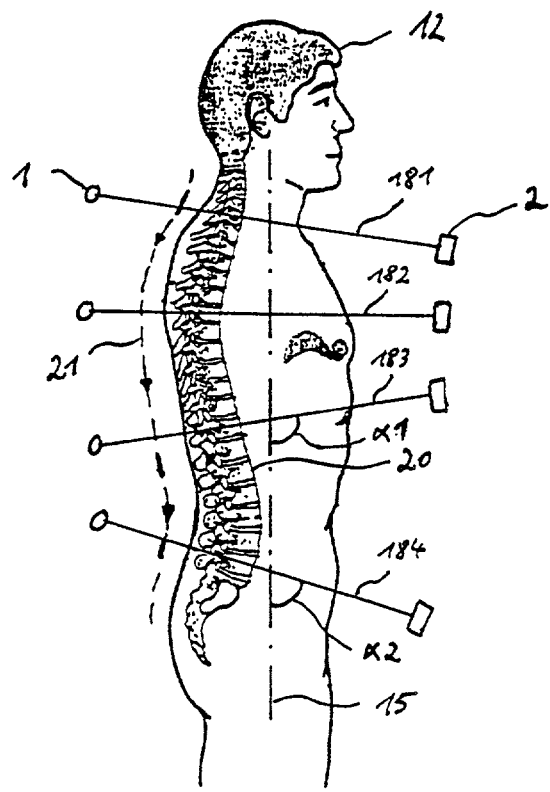
FIG. 3 illustrates the acquisition of frontal projection images in accordance with the invention.

FIG. 3 shows a first embodiment of the invention. Therein, frontal views of the spinal column 20 of the patient 12 are to be acquired. Preferably these frontal views are acquired when the patient 12 is in an upright position. According to the invention at first a lateral overview image, preferably with a low X-ray dose, is acquired as the at least one initial projection image which preferably includes the vertebral column 20 completely. The overview image is determined from several initial projection images of different portions of the spinal column 20. Therein the region of interest, for example, the complete spinal column 20 or portions thereof, can be indicated. Then the spinal axis line 21 is detected by known measures, and the lateral tilt angles α of the vertebrae of interest are measured by means of known methods. This information about the spinal axis line 21 and/or the tilt angles is used to generate a set of projection lines 181, 182, 183, 184 perpendicular to the axis line 21. As is indicated in FIG. 3, the tilt angle α1 for the projection line 183 deviates from the tilt angle α2 of the projection line 184. In general, the tilt angle is defined herein as the average angle of both endplates of a vertebra with respect to the patient axis 15. The angle between the projection line and the patient axis 15 is then made equal to this tilt angle for each vertebra.

Preferably, one projection line is determined for each vertebra in the region of interest. From all these projection lines (in FIG. 3 there are only four projection lines 181 to 184 shown but there will be more projection lines in practice) a scanning trajectory is generated along which the X-ray source 1 and the X-ray detector 2 are dynamically moved during the subsequent acquisition of projection images of the spinal column 20. Thus, the X-ray source 1 and the X-ray detector 2 are dynamically angulated so as to align with a projection line for each vertebral body. This results in a series of frontal projections that all extend as parallel as possible to the endplates of the vertebral body. This alleviates the well-known problem of low-quality frontal images for patients with large frontal or backward curves due to disturbing overprojections and due to the fact that the projections are far from parallel to the vertebral endplates.

The projection images acquired can be combined so as to form a composite image, this combination requiring an additional processing effort, or the projection images can be displayed separately. The angulation of each image is mentioned with the image as a rough indication of the lateral tilt angle and also to allow interpretation of the image.

Figure 4:
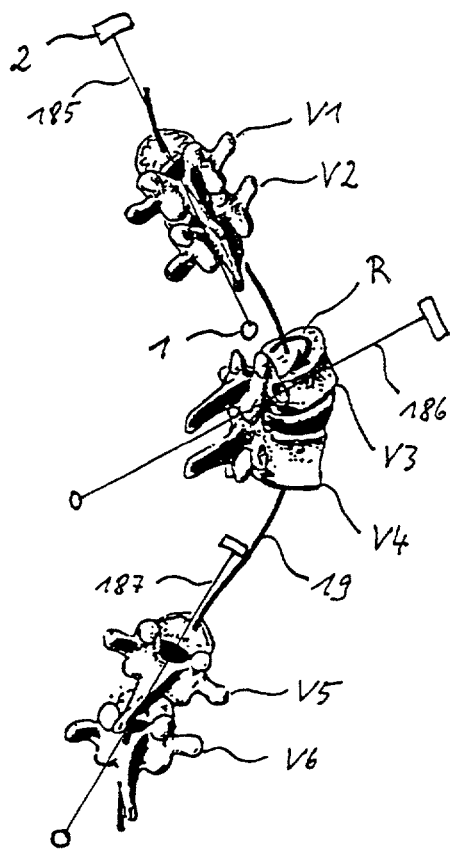
FIG. 4 illustrates the acquisition of projection images of an axially rotated spinal column in accordance with the invention.

Another embodiment of the invention will be explained with reference to FIG. 4. The spinal axis line 19 shown in FIG. 4 is curved in the lateral direction. Additionally the vertebrae V1-V6 are rotated around the spinal axis line 19 as indicated by the arrow R. The spinal column of a patient suffering from scoliosis typically exhibits such a curvature and such a rotation of the vertebrae.

According to the invention one or more initial frontal projection images are acquired first. Therefrom the axial rotation of the vertebrae is estimated or measured, that is, in particular by comparing the pedicle positions with respect to the vertebral body center. Using this information for each vertebra or for each group of vertebrae, projection images are acquired while rotating the source-detector unit so as to compensate for the axial rotation of the vertebrae. This results in views of the vertebrae with no or only a small axial rotation, for example, in real frontal views with respect to a local vertebra coordinate system. Acquisitions perpendicular to these minimal axial rotation views will result in real lateral views. A combination of the initial axial rotation estimate and the remaining small rotation will result in more accurate axial rotation measurements. As can be seen in FIG. 4, the projection lines 185, 186, 187 are rotated around the spinal axis line 19 independance on the rotation of the vertebra to be imaged along this projection line.

Figure 5:
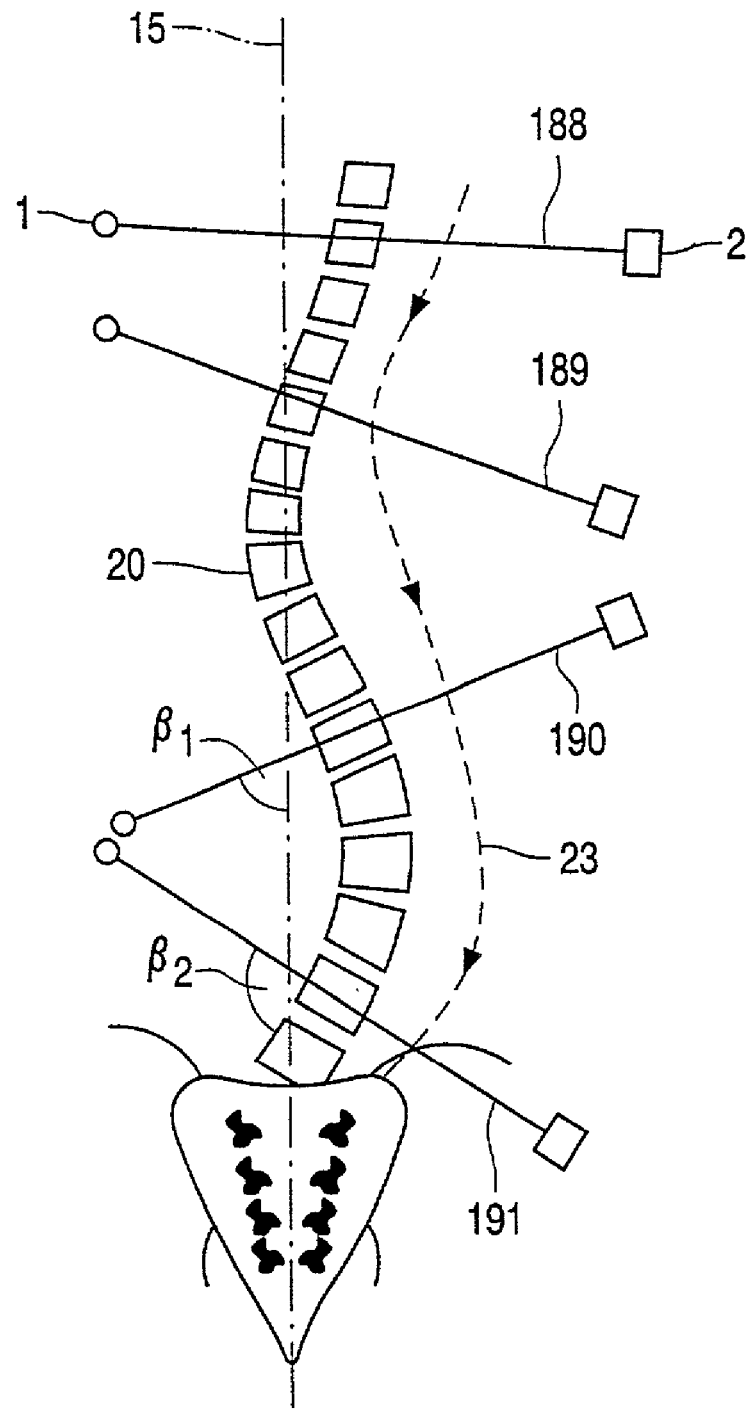
FIG. 5 illustrates the acquisition of lateral projection images in accordance with the invention.

A third embodiment will be explained in more detail with reference to FIG. 5. This Figure is a frontal view of the spinal column 20 having a double major curve. Such a curvature appears for patients suffering from scoliosis. In order to acquire high-quality lateral projection images first a frontal overview image is acquired. Preferably, the spinal axis line is shown therein, that is, completely or at least the region of interest of the spinal axis line. From the overview image the spinal axis line is detected or indicated and/or the frontal tilt angles β of some or all vertebrae of interest are measured. Using of this information or the tilt angles β a set of projection lines 188, 189, 190, 191 perpendicular to the spinal axis line is generated. Preferably, one projection line per vertebra is generated. The tilt angles β are defined therein as the angles between a projection line extending parallel to the endplates of the vertebra to be imaged, and the patient axis 15 as shown in FIG. 5. As can be clearly seen in this FIG., the tilt angles β1 and β2 are quite different due to the lateral curvature of the spine.

From the projection lines 188-191 a scanning trajectory 23 is generated along which the X-ray source 1 and the X-ray detector 2 are moved while acquiring projection images of the spinal column 20. Therefore, the source-detector unit is rotated to the lateral view, translated from start to stop position, and angulated dynamically so as to align with the projection lines for each vertebral body or for each group of vertebral bodies. This results in a series of lateral projections that are all as parallel as possible to the endplates of the vertebrae. This alleviates the well-known problem of low quality lateral images that are obtained for patients with large lateral curves; this is due to disturbing overprojections and due to the fact that the projections are far from parallel to the vertebral endplates.

Preferred embodiments of the invention have been explained above. However, the claims are not limited to these embodiments. Modifications and further embodiments of the invention are also possible. In particular, frontal and lateral overview images can be acquired to fit a three-dimensional spinal axis model to these images and to calculate therefrom an optimum three-dimensional scanning trajectory along which a series of images is acquired.

According to the invention the X-ray source and detector positions are controlled by image information in order to obtain an optimum view of specific parts of the spinal column automatically. The image information can be used for automatic optimum adjustment of the collimation, the exposure parameters and the projection orientation. An X-ray apparatus that is preferably used to execute this method should allow movements along two axes, for horizontal and vertical translation, and around at least two axes, meaning that it should allow rotation and angulation like a C-arm or a U-arm. Furthermore, the exposure, the collimation and the projection geometry should be fully controllable and registration of all image acquisition information like geometry, table position, exposure and collimation settings, should be possible. Preferably, it should be possible to determine acquisition settings using information that the operator or an automatic algorithm can derive from intermediate or overview images.

The invention claimed is:

1. A method for imaging a plurality of individual anatomical parts of the human anatomy by means of an X-ray apparatus, the method comprising the steps of:
   acquiring at least one initial projection image of at least a region of interest of the human anatomy and retaining acquisition settings for the at least one initial projection image,
   determining the positions and/or orientations for each of the plurality of individual anatomical parts in the region of interest from the at least one initial projection image,
   determining locally adapted optimum imaging parameters for each of the plurality of individual anatomical parts from (i) the determined positions and/or orientations of respective individual anatomical parts and (ii) the retained acquisition settings for the at least one initial projection image, wherein the locally adapted optimum imaging parameters include one or more settings of projection line position, projection line direction, collimation, and exposure, and acquiring projection images for each of the plurality of individual anatomical parts by dynamically using respective ones of the locally adapted optimum imaging parameters for each of the plurality of individual anatomical parts.

2. A method as claimed in claim 1, wherein optimum exposure and/or collimator settings are determined from the positions, orientations and/or appearance of the anatomical parts in the at least one initial projection image.

3. A method as claimed in claim 1, wherein optimum projection lines for acquiring projection images of the anatomical parts are determined from the positions and/or orientations of the anatomical parts.

4. A method as claimed in claim 1, wherein the at least one initial projection image is taken as a frontal image and/or a lateral image.

5. A method as claimed in claim 1, wherein the at least one initial projection image is an overview image reconstructed from at least two projection images.

6. A method as claimed in claim 1, wherein an optimum projection line is determined for each anatomical part in the region of interest.

7. A method as claimed in claim 1, wherein the acquired images of the anatomical parts are displayed separately or are combined to form a composite image for display.

8. A method as claimed in claim 1, wherein the method is used for imaging the human spine and comprises the steps of:
   acquiring at least one initial projection image of at least a region of interest of the spine and retaining acquisition settings for the at least one initial projection image,
   determining positions and/or orientations of each vertebrae in the region of interest from the at least one initial projection image,
   determining locally adapted optimum imaging parameters for each vertebrae from (i) the determined positions and/or orientations of respective vertebrae and (ii) the retained acquisition settings for the at least one initial projection image, and
   acquiring projection images of each vertebrae by dynamically using respective ones of the locally adapted optimum imaging parameters.

9. An X-ray apparatus for imaging a plurality of anatomical parts of the human anatomy of a patient, in particular parts of the human spine, having an x-ray source and an x-ray detector facing the x-ray source, the x-ray source and the x-ray detector being movable with respect to each other and with respect to the patient so as to enable the acquisition of projection images of each of the plurality of anatomical parts from different positions and/or orientations, the x-ray apparatus comprising:
   a control unit for controlling the x-ray apparatus to acquire at least one initial projection image of at least a region of interest of the human anatomy and to retain acquisition settings for the at least one initial projection image, and
   a processing unit for determining the position and/or orientation of individual anatomical parts in the region of interest from the at least one initial projection image and for determining locally adapted optimum imaging parameters for each of the plurality of individual anatomical parts from (i) the determined positions and/or orientations of respective individual anatomical parts and (ii) the retained acquisition settings for the at least one initial projection image, wherein the locally adapted optimum imaging parameters include one or more settings of projection line position, projection line direction, collimation, and exposure, the control unit further for controlling the x-ray apparatus to acquire projection images of each of the individual anatomical parts by dynamically using respective ones of the locally adapted optimum imaging parameters.

10. A method for imaging the human spine comprising the steps of:
   acquiring at least one initial projection image of at least a region of interest of the spine and retaining acquisition settings for the at least one initial projection image,
   determining positions and/or orientations of each vertebrae in the region of interest from the at least one initial projection image, the positions and/or orientations including a spinal axis line and a tilt angle per vertebrae,
   determining locally adapted optimum imaging parameters French of the vertebrae from (i) the determined positions and/or orientations of respective vertebrae and (ii) the retained acquisition settings for the at least one initial projection image, wherein the locally adapted optimum imaging parameters include one or more settings of projection line position, projection line direction, collimation, and exposure, and
   acquiring projection images of each of the vertebrae while by dynamically using the corresponding locally adapted optimum imaging parameters for each respective vertebrae.

11. A method as claimed in claim 1, further comprising the step of generating a scanning trajectory prior to the step of acquiring images, and wherein the step of acquiring images of the plurality of anatomical parts includes the step of moving at least one device along the scanning trajectory.

12. A method as claimed in claim 6, further comprising the step of generating a scanning trajectory using the optimum projection line determined for each anatomical part in the region of interest, prior to the acquiring images step.

13. A method as claimed in claim 9, wherein the x-ray source and x-ray detector are moved along a scanning trajectory for acquiring the images.

14. A method as claimed in claim 10, further comprising the step of generating a scanning trajectory prior to the step of acquiring images, and wherein the step of acquiring images of each of the vertebrae includes the step of moving at least one device along the scanning trajectory.

* * * * *